United States Patent [19]
DiMarchi et al.

[11] Patent Number: 5,422,426
[45] Date of Patent: Jun. 6, 1995

[54] RAPID SYNTHESIS AND SCREENING OF PEPTIDE MIMETICS

[75] Inventors: Richard D. DiMarchi, Carmel; Paul D. Gesellchen; Rebecca A. Owens, both of Indianapolis, all of Ind.

[73] Assignee: Eli Lilly and Company, Indianapolis, Ind.

[21] Appl. No.: 67,279

[22] Filed: May 25, 1993

Related U.S. Application Data

[63] Continuation of Ser. No. 717,184, Jun. 18, 1991, abandoned.

[51] Int. Cl.$^6$ .............................. C07K 1/04; C07K 1/06
[52] U.S. Cl. .................................. 530/334; 530/333; 525/54.11
[58] Field of Search .......................... 530/334, 333; 525/54.11

[56] References Cited

U.S. PATENT DOCUMENTS

| | | | |
|---|---|---|---|
| 4,631,211 | 12/1986 | Houghten | 428/35 |
| 4,833,092 | 5/1989 | Geysen | 436/501 |
| 5,010,175 | 4/1991 | Rutter et al. | 530/334 |
| 5,182,366 | 1/1993 | Huebner et al. | 530/334 |
| 5,266,684 | 11/1993 | Rutter et al. | 530/334 |

FOREIGN PATENT DOCUMENTS

| | | |
|---|---|---|
| 0383620 | 8/1990 | European Pat. Off. |
| 260634 | 9/1987 | Germany |
| 272856 | 6/1988 | Germany |
| WO86/00991 | 2/1986 | WIPO |
| WO86/06487 | 11/1986 | WIPO |

OTHER PUBLICATIONS

Houghten, *Proc. Natl. Acad. Sci.*, 82, 5131–5135 (1985).
Furka, et al., *Int. J. Peptide Protein Res.*, 37, 487–493 (1991).
Tjoeng, et al., *Int. J. Peptide Protein Res.*, 35, 141–146 (1990).
Geysen et al., *Proc. Natl. Acad. Sci.*, 81, 3998–40002 (1984).
Scott et al., *Science*, 249, 386–249 (1990).
Furka et al., (1988, 14th Int'l Congress of Biochemistry vol. 5, Abstract FR:013).
Furka et al., *Xth International Symposium on Medicinal Chemistry*, Abstracts, Budapest, Hungary, Aug. 15–19, 1988.
Furka et al., "More Peptides By Less Labour", Poster Presentation at Xth International Symposium on Medical Chemistry, Budapest, Hungary, Aug. 15–19, 1988.
Furka et al., "Cornucopia of Peptides by Synthesis", Poster Presentation at 14th International Congress of Biochemistry, Prague, Czechoslovakia, Jul. 10–15, 1988.

*Primary Examiner*—Jill Warden
*Assistant Examiner*—Carol A. Salata
*Attorney, Agent, or Firm*—Paul R. Cantrell; Gerald V. Dahling

[57] ABSTRACT

A method is disclosed for the rapid synthesis of very large numbers of peptides which can be integrated with the screening of these peptides as heterogeneous mixtures to identify the specific peptides which demonstrate biological activity using a small number of coupling steps.

9 Claims, No Drawings

RAPID SYNTHESIS AND SCREENING OF PEPTIDE MIMETICS

This application is a continuation of application Ser. No. 07/717,184, filed Jun. 18, 1991, now abandoned.

BACKGROUND OF THE INVENTION

An approach has been developed for the rapid synthesis and screening of large numbers of small peptides with the aim of producing a molecule which mimics the high binding affinity and specificity of the larger natural ligands for enzymes and cellular receptors. Molecules with these attributes have been termed "mimetics" which have potential for many uses. For example, mimetics are attractive as therapeutic agents because they represent easily synthesized molecules. The current process represents an alternate strategy to the systematic alteration of natural ligands, which has proven slow and difficult, and the low probability approach of randomly screening compounds which do not have any known structural similarity to the natural ligand. The process makes possible the rapid simultaneous production of peptides in numbers larger than has been previously achieved by conventional solid phase synthetic methods and provides a way to readily determine and synthesize in pure form the specific sequences which are responsible for a desired activity.

The current process provides for several important advances over the prior art. Several reports using comparable solid-phase techniques show synthesis to be practically limited to several hundred peptides made at a time while the current process provides for the synthesis of peptides in virtually unlimited number.

Other recent reports, which accomplish production of very high numbers of small peptides in a short period of time using solid-phase technology, disclose the coupling of mixtures of amino acids to growing peptide chains. That approach requires regulation of the concentration of the amino acids in the mixtures to account for differing relative coupling rates of the amino acids in order that the concentrations of the resulting peptides are equal. In addition, that approach requires the application of multiple analytical techniques in order to determine the precise sequence which is responsible for the desired activity. The current process differs in that a single amino acid or group of amino acids is coupled at each coupling step obviating the need to account for differing coupling rates of the amino acids and ensuring the production of peptides in equimolar amounts. The current process also allows identification of the desired sequence and subsequent production in pure form without chemical analysis.

Still other reports teach inserting randomly synthesized oligonucleotides into filamentous phage. This biosynthetic method potentially allows the production of millions of small peptides, which, however, must be limited to genetically encoded amino acids and which can only have a linear configuration. The current invention allows for the inclusion of D-amino acids or otherwise modified amino acids and the synthesis of branched chain sequences, neither of which is possible with recombinant DNA methods.

Perhaps most importantly, in contrast to teachings in the prior art, the current process allows for evaluation of the peptides' ability to interact with the target binding site without the potential interference of the support resin. In short, this invention enables the production of a very large number of small peptides and provides the ability to readily identify the specific peptide or peptides which demonstrate a desired activity and to produce them in pure form.

SUMMARY OF THE INVENTION

The present invention discloses a process for the rapid synthesis and screening of very large numbers of small peptides. The invention enhances the ability to produce a molecule which mimics the high binding affinity and specificity of the natural ligands for enzymes and receptors by generating mixtures of small peptides. By the nature of the process, the concentration of each selected amino acid at each position in the mixture, and, therefore, the concentration of each peptide, is held closely to within prescribed ratios. The process allows production of peptide mixtures which can be tested free of a support resin without losing the ability to readily identify the specific peptide or peptides which are responsible for a desired activity. The peptide mixtures are made up of a series of peptides which contain a common amino acid at the last coupled position, and perhaps at other expressly selected positions, but where all of the other residues are a random selection of different amino acids. For purposes of the current invention, a peptide sequence made by the current process can have either a linear or branched chain structure.

The present invention comprises a method of synthesizing a very high number of peptides within peptide mixtures comprising: doing a first synthesis of peptide mixtures, each made up of n amino acids or groups of amino acids, by n synthetic steps of which the first synthetic step consists of coupling to completion, amino acids or groups of amino acids individually to aliquots of solid-support resin; and the additional steps each consist of thoroughly mixing the aliquots of resin-coupled amino acids or groups of amino acids; dividing the mixture into equal aliquots; coupling to completion, amino acids or groups of amino acids individually to each of the aliquots; and if desired, cleaving the peptides from the resins in each mixture so as to produce peptide mixtures each member of which has a known amino acid at the last coupled position.

This synthetic process may be integrated with a biological assay in order to determine the sequence of a particular peptide or peptides which have biological activity. The integrated process further comprises:

A. doing a first assay of each peptide mixture for biological activity thereby completing a first synthetic cycle;

B. doing a second synthesis of the peptides using the same amino acids or groups of amino acids used in the first synthesis at each of the n coupling steps by repeating the first synthesis through steps n-1; and, in step n, coupling to completion, the amino acid or group of amino acids, appearing at the terminus of the peptide mixture which demonstrated biological activity in the first assay, to each of the peptide mixtures; if desired, cleaving the peptides from the resins in each mixture; doing a second assay of each peptide mixture for biological activity thereby completing a second synthetic cycle; and C. performing the steps of the synthetic cycle a total of n times so as to synthesize a peptide of fully known sequence.

It should be noted that the present invention includes the ability to make peptides with branching peptide side chains by the same rapid synthetic process. These branching molecules, made as mixtures, may also be assayed for activity and the sequence of a specific molecule or molecules having activity may be identified in essentially the same manner as linear peptides.

For purposes of the present invention, as disclosed and claimed herein, the following terms and abbreviations are as defined below.

Terms and Abbreviations

Ac—acetyl
Bzl—benzyl
0-Bzl—benzyl ester
Bom—benzyloxymethyl
Tos—tosyl[4-toluenesulfonyl]
2Cl-Z—2-chlorobenzyloxycarbonyl
2,6Cl-Z—2,6-dichlorobenzyloxycarbonyl
2Br-Z—2-bromobenzyloxycarbonyl
X—an amino acid whose identity is unknown L-amino acids are herein indicated by capitalizing the first letter in their standard three letter codes and D-amino acids are denoted by using all small letters in their standard three letter codes.

DETAILED DESCRIPTION OF THE INVENTION

The current invention can be practiced using solid phase synthetic procedures which are routinely applied in peptide synthesis. In general, an amino acid which will ultimately correspond to the C-terminal amino acid residue of the resulting peptide is anchored to an insoluble support resin by means of a covalent linkage formed between the carboxyl group of the C-terminal residue and a specific functional group present on the resin matrix as a site of attachment. The peptide then is formed, beginning at the resin-coupled C-terminal amino acid, by coupling to an amino group at an N-terminal residue of the peptide in successive order. There may be more than one N-terminal residue if a branched structure is present. The peptide remains attached to the resin throughout the synthesis but may be cleaved from the resin once the complete peptide sequence is assembled.

A process to produce peptides containing from 2 to about 8 amino acids or groups of amino acids is a particularly preferred embodiment of the invention.

The new process is based on the repeated mixing, dividing, and coupling of resin-coupled amino acids or peptides. The first step requires the dividing of solid-support resin into aliquots having equal amounts of attachment sites. This is followed by coupling to completion of individually selected amino acids to each aliquot, each aliquot of resin being coupled to a different amino acid. As a result, the resin in each aliquot will be coupled to the same molar amount of amino acid as other aliquots which are coupled to different amino acids. The resins are thoroughly mixed to produce an equimolar mixture of resin-coupled am/no acids. The mixture is then divided into equal aliquots followed by further coupling of individually selected amino acids to the resin-coupled amino acids in each aliquot. Repeated stepwise mixing, dividing, and coupling steps result in peptide mixtures where the last-coupled amino acid residue is the same for all peptides in a given mixture but where the amino acid residues at all other positions of each peptide in the mixture represent an equimolar selection of the amino acids which were included in a given coupling step.

As an alternative, a single amino acid may be coupled at any given coupling step so that all of the peptides synthesized will have the same amino acid at a given position. When this is done, the dividing step immediately preceeding the coupling step and the mixing step immediately following the coupling step may be eliminated. This results in peptide mixtures as before but where the identity of an amino acid at a given position, in addition to the last-coupled position, is known.

This process generates very large numbers of peptides in amounts suitable for biological assay using a small number of coupling steps. As a result, every possible sequence is made which can be made from the use of the selected amino acids. For example, if 25 amino acids are selected for the synthesis of peptides, 625 dipeptides are produced after only 50 coupling steps done in two successive rounds of 25 reactions; 15,625 tripeprides are produced after 75 coupling steps done in three rounds of reactions; and 390,625 unique tetrapeptides are produced after only 100 coupling steps done in four rounds of reactions. Using greater numbers of coupling steps to produce longer peptides would result in even larger numbers of peptides within a mixture.

The number and type of amino acids selected for use in the synthesis may be varied from one round to the next and may reflect a random selection without any presumptions about which amino acids are most appropriate or may include a particular selection of certain amino acids based on features known to affect a desired activity.

The number of successive couplings which can be accomplished with this method is subject only to those factors known in the art to limit solid-phase synthesis of peptides. However, it should be noted that increasing the number of peptides within a mixture decreases the amount of each peptide as a fraction of the total peptide concentration. Therefore, when the synthesis of peptide mixtures is integrated with a biological assay to determine the sequence of the active peptide as described below, assay sensitivity must be considered in deciding the number of couplings which can be done practically. That is, the ability of the assay to recognize a signal of activity from perhaps a single peptide over the "noise" of the great excess of inactive mixture constituents will be a limiting factor in the number of peptides which can be contained within a mixture that is to be tested for activity. The solubility of the peptides within a mixture also reflects on this same consideration of the practical limit of peptides which can be synthesized when an assay is used to detect activity of peptides within a mixture.

when this method for producing peptides is combined with a biological assay, the specific sequence of the peptide or peptides within a mixture having activity are readily identified and subsequently produced in pure form. The peptides may first be cleaved from the resin before being assayed for biological activity. Cleaving the peptides from the resin eliminates the possibility of interference with the activity of the peptides due to such factors as, for example, steric hindrance. The peptides are then submitted as mixtures to the biological assay. Since each peptide within a mixture has a known amino acid residue at the last coupled position, an assay which reveals a mixture as having activity necessarily identifies the amino acid residue at the last coupled site. The overall procedure of synthesizing peptide mixtures and assaying for activity is termed a "synthetic cycle".

In order to identify the specific sequence of the peptide or peptides within a mixture which are responsible for the observed activity, all of the peptides within the mixture having activity, as determined by assay during the first synthetic cycle, are resynthesized by the same mixing, dividing, and coupling procedure but in this second synthetic cycle the peptide mixtures are not mixed after the penultimate coupling. Thus, the identity of the Penultimately-coupled amino acid is known for a given mixture. The last-coupled amino acid identified by the biological assay of the previous synthetic cycle is then coupled to the peptides in each mixture so that the identity of the last two coupled amino acid residues is known for all peptides in a given peptide mixture. The mixtures are again submitted to the biological assay to identify the mixture which demonstrates activity. As a result, the identity of two amino acid residues of the peptide responsible for the observed activity is determined. The process of resynthesizing the peptide mixture having the desired activity and resubmitting the mixture for assay is repeated thereby identifying an additional amino acid residue with each synthetic cycle until the sequence of the peptide responsible for the activity found in the mixture is fully elucidated.

Starting resins may be generated as described below or may be purchased from commercial sources with amino acids already conjugated to them. Amino acids which are purchased in an already resin-coupled form substitute for the first synthetic coupling step described in the summary of the invention. In addition to the procedure for producing peptides from individual amino acids, a group of amino acids can be coupled at any or all of the coupling steps. A group of amino acids is simply a peptide of known sequence which can be coupled as described within this disclosure. Thus, the multiple peptide synthesis and screening technique can be used to generate peptide mixtures by lengthening known peptide sequences at the N-terminus, the C-terminus, or both and to identify the resulting sequence which possesses activity. In addition, as already mentioned, peptide sequences made by this procedure may have a branching configuration.

The amino acids are coupled using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethyl chloroformate, phenyl chloroformate, sec-butyl chloroformate, or isobutyl chloroformate. Alternatively, the amino acid can be converted to an active ester such as a 2,4,5,-trichlorophenyl ester, a pentachlorophenyl ester, a pentafluorophenyl ester, a p-nitrophenyl ester, an N-butyloxycarbonyl ester (t-Boc), an N-hydroxysuccinimide ester, or an ester formed from 1-hydroxybenzotriazole.

Another coupling method involves use of a suitable coupling agent, such as N,N'-dicyclohexylcarbodiimide (DCC) or N,N'-diisopropylcarbodiimide (DIC). Other appropriate coupling agents will be apparent to those skilled in the art. See Schroder and Lubke, The Peptides, Academic Press, 1965, Chapter III and U.S. Pat. No. 4,259,234.

It should be recognized that the alpha-amino group of each amino acid employed in the peptide synthesis must be protected during the coupling reaction to prevent side reactions involving the reactive alpha-amino function. It should also be recognized that certain amino acids contain reactive side-chain functional groups (e.g. sulfhydryl, epsilon-amino, beta- and gamma- carboxyl, imidazole, guanidino and hydroxyl) and that such functional groups must also be protected both during the initial and subsequent coupling steps. Suitable protecting groups are known in the art. See for example, Protective Groups in Organic Chemistry, M. McOmie, Ed., Plenum Press, N.Y., 1973 and U.S. Pat. No. 4,617,149.

In selecting a particular protecting group, certain conditions must be observed. An alpha-amino protecting group must render the alpha-amino function inert under the conditions employed in the coupling reaction, it must be readily removable after the coupling reaction under conditions that will not remove side chain protecting groups and which will not alter the structure of the peptide fragment, and the alpha-amino protecting group must eliminate the possibility of racemization upon activation immediately prior to coupling. A side chain protecting group must render the side chain functional group inert under the conditions employed in the coupling reaction, it must be stable under the conditions employed in removing the alpha-amino protecting group, and it must be readily removable, if necessary, upon completion of the peptide under conditions that will not alter the structure of the peptide chain.

It will be apparent to those skilled in the art that the protecting groups known to be useful for peptide synthesis will vary in reactivity to the agents employed for their removal. For example, certain protecting groups, such as triphenylmethyl and 2-(p-biphenylyl)isopropyloxycarbonyl are very labile and can be cleaved under mild conditions. Other protecting groups, such as t-butyloxycarbonyl, t-amyloxycarbonyl, adamantyloxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl, halobenzyloxycarbonyl, p-nitrobenzyloxycarbonyl, cycloalkyloxycarbonyl, and isopropyloxycarbonyl are even less labile and require stronger acids, such as hydrogen fluoride (HF), hydrogen bromide, or boron trifluoroacetate in trifluoroacetic acid, for their removal. 9-Fluoroenylmethyloxycarbonyl (Fmoc) protecting groups may also be used and are readily removed by piperidine under conditions which leave other protecting groups intact.

Upon completion of the coupling steps, the protected peptide may be cleaved from the resin support and all protecting groups may be removed. The cleavage reaction and removal of the protecting groups may be accomplished simultaneously or stepwise. When the resin support is a chloromethylated polystyrene resin, the bond anchoring the peptide to the resin is an ester linkage formed between the free carboxyl group of the C-terminal moiety and one of the many chloromethyl groups present on the resin matrix. It will be recognized that the anchoring bond can be cleaved by reagents which are known to be capable of breaking an ester linkage and of penetrating the resin matrix. One especially convenient method is by treatment with liquid anhydrous HF. This reagent not only will cleave the peptide from the resin but may also remove all protecting groups. Hence, use of this reagent will directly afford the fully deprotected peptide. When it is desired to cleave the peptide without removing protecting groups, the protected peptide-resin can undergo methanolysis to give the protected peptide in which the C-terminal carboxyl group is methylated. The methyl ester can then be hydrolyzed under mild, alkaline conditions to give the free C-terminal carboxyl. The protecting groups on the peptide chain then can be removed by treatment with a strong acid, such as liquid HF. A particularly useful technique for the creation of peptides like those of this invention is described in Hui, K. Y. et al., 1988, J. Med. Chem. 31, 1679–1686.

Another method for cleaving the protected peptide from the resin is by ammonolysis or by treatment with hydrazine. It will also be recognized that the protecting group present on the N-terminal alpha-amino group may be removed preferentially either before or simultaneously with the cleavage of the protected peptide from the resin support.

Skilled artisans will recognize that the scheme introduced here can be used with any solid phase chemistry known or developed with all combinations of amino acids and derivatives to produce peptides of any length or sequence. In order to generate branching molecules, amino acids or chains of amino acids may be coupled to a second amino group which exists on a residue of the first chain. For example, amino acids such as lysine can be coupled at some point common to all of the growing peptides in order that an amino acid or group of amino acids may be attached to a second amino group which is on the amino acid. Alternatively, modified amino acids may be synthesized to have two or more amino groups so that the amino acid can serve as a branching point. These side branches can then be lengthened by the same mixing, dividing, and coupling described for linear molecules. When branching molecules are made, the protecting groups on the side branches must be different from the protecting groups which are used in building the first branch. For example, using t-Boc protecting groups on one branch and Fmoc protecting groups on another branch allows the selective manipulation of the different branches using different conditions and deprotecting reagents.

Many naturally occurring and non-naturally occurring amino acids are commercially available, in both the protected and unprotected form, from a wide variety of sources. Other amino acids which might not be available from commercial sources may be synthesized. All of the reagents and materials necessary to practice this invention are available from Advanced ChemTech (PO Box 1403, Louisville, Ky.) or Applied Biosystems (850 Lincoln Center Dr., Foster City, Calif.) unless specified otherwise.

This invention is not dependent upon any specific assay for biological activity. Any assay capable of recognizing any desirable activity of peptides can be used as a part of the current process to identify and produce the specific peptide or peptides within a peptide mixture which are responsible for the desired activity. Common assays might include receptor-ligand binding, immunological reactivity, or effects on enzyme activity.

The techniques and sources set forth in the Examples are provided as a means of illustrating the invention and are not to be construed as a limitation thereon.

EXAMPLE 1

C-Terminally amidated peptides were synthesized on p-methylbenzhydrylamine (p-MBHA) resin using a RAMPS ™ (DuPOnt, 549 Albany St., Boston, Mass.) multiple peptide synthesis apparatus. The amino acids used had t-BoC alpha-amino protecting groups and side chains were protected as follows: Asp (O-Bzl), Glu (O-Bzl), Ser (Bzl), His (Bom), Lys(2Cl-Z), D-Tyr(2,6Cl-Z), and Arg(Tos). The RAMPS ™ apparatus is basically a manifold whereby a vacuum can be applied simultaneously to a number of polypropylene reaction vessels for aspiration of solvents and soluble reagents such as uncoupled amino acids. These reaction vessels, termed cartridges, have a valve for controlling the application of a vacuum and a "polyball" which retains the support resin, along with any coupled amino acids or peptides, within the cartridge upon aspiration, thus facilitating the separation, washing, neutralization, and deprotection steps of the synthesis.

Twenty-two cartridges each received 0.2 grams of p-MBHA resin having about 0.6 mmoles of amine attachment sites per gram of resin. The amine attachment sites were neutralized with 10% diisopropylethylamine (DIEA) in dimethylformamide (DMF). Four equivalents (4 moles/mole resin amine) of each t-Boc-amino acid listed in Table 1 was dissolved in 1 ml DMF and added to the cartridges, each cartridge receiving a different t-Boc-amino acid. Four equivalents of 0.5M 1-hydroxybenzotriazole (HOBt) in DMF were then added to the cartridges followed by 4 equivalents of diisopropylcarbodiimide (DIC). The cartridges were rocked end-over-end for 60 minutes followed by washing, neutralization, and recoupling with the same amino acid under the same conditions and concentrations. This second coupling is necessary to ensure that all attachment sites on the resin are coupled. The coupling reactions were tested for completeness by ninhydrin analysis before continuing to the next amino acid. The t-BoC-amino acids were deprotected by treatment for 30 minutes with 50% trifluoroacetic acid (TFA), 5% anisole, and 45% methylene chloride. The coupled resins were removed from each of the cartridges and thoroughly mixed, thus producing a mixture where the molar amount of each amino acid coupled at the first position was the same.

The resin-coupled amino acid mixture was divided evenly into 23 cartridges. The 22 t-Boc-amino acids listed in Table 1 plus the transition-state t-Boc-amino acid statine (Sta) were then coupled to the amino acid mixture aliquots, each aliquot being coupled with a different t-Boc-amino acid. This coupling, done as described above, produced 23 peptide mixtures, each of which had 22 different resin-coupled dipeptides where the amino acid residue at the N-terminus was known. Two rounds of coupling reactions produced 506 unique dipeptides. The coupling reactions were again tested for completeness before deprotection. The resin-coupled dipeptides were removed from the cartridges and thoroughly mixed to produce dipeptide mixtures where the molar amount of each amino acid coupled at each position was the same.

The resin-coupled dipeptide was divided evenly into 22 cartridges. The 22 t-Boc-amino acids listed in Table 1 were then coupled to the dipeptide mixture aliquots, each aliquot being coupled with a different t-Boc-amino acid. This coupling, done as described above except that the t-Boc-amino acid was added last to prevent diketopiperazine formation which may occur upon deprotection, produced 22 peptide mixtures which each had 506 different resin-coupled tripeprides where the amino acid residue at the N-terminus was known. Three rounds of coupling reaction produced 11,132 unique tripeprides. The coupling reactions were again tested for completeness before deprotection. The resin-coupled tripeprides were removed from the cartridges and thoroughly mixed to produce tripeptide mixtures where the molar amount of each amino acid coupled at each position was the same.

The resin-coupled tripeptide mixture was divided evenly into 22 cartridges. The 22 t-Boc-amino acids listed in Table 1 were then coupled to the tripeptide mixture aliquots, each aliquot being coupled with a different t-BOC-amino acid. This coupling, done as described for the first coupling, produced 22 peptide mixtures which each had 11,132 different resin-coupled tetrapeptides where the amino acid residue at the N-terminus was known. Four rounds of coupling reactions produced 244,904 unique tetrapeptides. The coupling reactions were again tested for completeness. The tetrapeptides were incubated for 2 hours in 10 equivalents of acetic acid, HOBt, and DIC in order to acetylate the N-terminal residue. The resin coupled acetylated tetrapeptides were removed from the cartridges but, unlike previous steps, the peptide mixtures produced in each cartridge were kept separate. Therefore, all of the tetrapeptides which came from a common cartridge had the same amino acid coupled at the N-terminus but all other residues of the chain represented random equimolar selections of each of the amino acids coupled in a given step. Thus, the tetrapeptides from each cartridge represented an equimolar mixture of every possible sequence which could have been produced with the selected amino acids while holding the N-terminal residue constant.

The tetrapeptides were washed with dichloromethane and dried at room temperature. The tetrapeptides were then cleaved from the MBHA resin in 90% liquid anhydrous HF/5% p-thiocresol/5% m-cresol at 0° C. for 70 minutes. This treatment also removed all of the side-chain protecting groups. The HF was distilled off and the cleaved tetrapeptides were precipitated with 50 ml of diethyl ether for 30 minutes at 0° C. Glass sintered funnels were used to collect the cleaved tetrapeptides and spent resin, followed by 4×20 ml washes with diethyl ether in order to precipitate the tetrapeptides. The precipitated tetrapeptides were dissolved in 50% acetic acid/30% acetonitrile and filtered into round bottom flasks. Approximately 70% of the volume was removed by vacuum distillation and the remaining portion was diluted with water and lyophilized. The dry weight of peptide recovered was determined and the mixtures were redissolved in 50% acetic acid/30% acetonitrile before dividing into small aliquots.

TABLE 1

| L-amino acids | D-amino acids |
|---|---|
| arginine | alanine |
| aspartic acid | asparagine |
| glutamine | glutamic acid |
| histidine | leucine |
| isoleucine | lysine |
| lysine | phenylalanine |
| phenylalanine | proline |
| proline | tryptophan |
| methionine | tyrosine |
| serine | valine |
| tyrosine | |
| tryptophan | |

EXAMPLE 2

The tetrapeptide mixtures generated in Example 1 were submitted to an assay which measured the ability of the peptides to inhibit the proteolytic activity of the human immunodeficiency virus (HIV-1) aspartyl protease. A critical step in the replicative cycle of HIV-1 is the proteolytic processing of certain polyprotein products which are encoded by the viral genome. The precursor proteins are cleaved to form mature proteins necessary for the retroviral life cycle. Therefore, compounds which act to inhibit the HIV-1 protease may play an important role as therapeutic agents in the management of Acquired Immunodeficiency Syndrome (AIDS).

The tetrapeptide mixtures were each diluted in dimethylsulfoxide (DMSO) before testing such that the total peptide concentration was about 15,585 uM in the assay. Since there were 11,132 unique tetrapeptides in each mixture, each individual tetrapeptide was essentially uM in the assay. Results are reported as percent inhibition of enzyme activity as compared to control measurements of cleaved substrate treated and untreated with proteolytic enzyme. AS shown in Table 2, several tetrapeptide mixtures demonstrated a significant ability to inhibit proteolytic activity. The tetrapeptide mixture which had a Phe residue at the N-terminus inhibited protease activity 103% and was selected for the resynthetic process in order to fully elucidate the sequence of the specific peptide or peptides which were responsible for the observed activity.

The tetrapeptides which had a Phe residue at the N-terminus were then resynthesized in the same manner and using the same set of amino acids described in Example 1 except that after the third coupling step the tripeptide mixtures were not mixed together, resulting in tripeptide mixtures where the identity of the amino acid at the third coupled position was known. Each tripeptide mixture was then coupled with Phe to produce 22 resin-coupled tetrapeptide mixtures which had two amino acids at the N-terminus whose identity was known. These tetrapeptide mixtures were cleaved and prepared for assay as described in Example 1. The tetrapeptide mixtures were each diluted in DMSO before submitting to the protease assay. The total peptide concentration was 5,060 uM in the assay such that each of the 506 unique tetrapeptides within each mixture was 10 uM. Table 2 indicates that the tetrapeptide mixture which had Phe-Ile at the N-terminus inhibited the protease activity by 68%.

The tetrapeptides which had Phe-Ile at the N-terminus were then resynthesized essentially in accordance with Example 1 but modified as described above so that the sequence of the three amino acids at the N-terminus was known. Each of the 23 tetrapeptide mixtures, each containing 22 unique tetrapeptides, were resubmitted to the protease assay as before. The total peptide concentration was 220 uM in the assay such that each of the 22 unique tetrapeptides within each mixture was 10 uM. Tetrapeptides mixtures with Phe-Ile-Sta at the N-terminus inhibited the protease activity 83% as indicated in Table 2.

TABLE 2

| ASSAY RESULTS FOR DEFINED SEQUENCES OF Ac—Phe—X—X—X—NH$_2$ | | | | |
|---|---|---|---|---|
| KWN = Known Residue | KWN—X—X—X | Phe—KWN—X—X | Phe—Ile—KWN—X | Phe—Ile—Sta—KWN |
| Arg | 17 | 0 | 8 | 8 |

TABLE 2-continued

ASSAY RESULTS FOR DEFINED SEQUENCES OF Ac—Phe—X—X—X—NH$_2$

| KWN = Known Residue | KWN—X—X—X | Phe—KWN—X—X | Phe—Ile—KWN—X | Phe—Ile—Sta—KWN |
|---|---|---|---|---|
| Ala | 11 | 0 | | 6 |
| Asp | 117 | 0 | 15 | 0 |
| Gln | 58 | 0 | 18 | 0 |
| His | 8 | 0 | 21 | 0 |
| Ile | 102 | 68.0 | 21 | 0 |
| Leu | 51 | 0 | 18 | 68 |
| Lys | 29 | 0 | 16 | 0 |
| Val | 30 | 28 | 15 | 1 |
| Phe | 57 | 23 | 15 | 43 |
| Phe | 103 | 7 | 16 | 0 |
| Pro | 9 | 0 | 17 | 0 |
| Met | 96 | 5 | 19 | 0 |
| Ser | 17 | 0 | 18 | 0 |
| Tyr | 98 | 8 | 4 | 0 |
| Trp | 65 | 6 | 7 | 19 |
| Trp | 81 | 9 | 1 | 0 |
| Lys | 5 | 0 | 0 | 0 |
| Pro | 9 | 0 | 21 | 0 |
| Tyr | 68 | 5 | 14 | 0 |
| Glu | 78 | 0 | 15 | 9 |
| Asn | 27 | 0 | 14 | |
| Sta | | | 83.0 | |

Each of the 22 tetrapeptides with Phe-Ile-Sta at the N-terminus were resynthesized essentially in accordance with Example 1 and resubmitted to the protease assay. As shown in Table 2, the tetrapeptide Phe-Ile-Sta-leu was the most potent tetrapeptide inhibiting protease activity 68%.

We claim:

1. A method of synthesizing a high activity peptide comprising:

A. doing a first synthesis of peptide mixtures, each made up of n amino acids or groups of amino acids, by n synthetic steps of which the first synthetic step consists of coupling to completion, amino acids or groups of amino acids individually to aliquots of solid-support resin; and the additional steps each consist of thoroughly mixing the aliquots of resin-coupled amino acids or groups of amino acids; dividing the mixture into equal aliquots; coupling to completion, amino acids or groups of amino acids individually to each of the aliquots; if desired, cleaving the peptides from the resins in each mixture so as to produce peptide mixtures each member of which has a known amino acid at the last-coupled position; and doing a first assay of each peptide mixture for biological activity thereby completing a first synthetic cycle;

B. doing a second synthesis of the peptides using the same amino acids or groups of amino acids used in the first synthesis at each of the n coupling step by repeating the first synthesis through steps n-1; and, in step n, coupling to completion, the amino acid or group of amino acids, appearing at the terminus of the peptide mixture which demonstrated biological activity in the first assay, to each of the peptide mixtures; if desired, cleaving the peptides from the resins in each mixture; doing a second assay of each peptide mixture for biological activity thereby completing a second synthetic cycle; and C. performing the steps of the synthetic cycle a total of n times so as to synthesize a peptide of fully known sequence.

2. A method of claim 1 wherein n is 2 to 8.
3. A method of claim 1 wherein n is 2.
4. A method of claim 1 wherein n is 3.
5. A method of claim 1 wherein n is 4.
6. A method of claim 1 wherein n is 5.
7. A method of claim 1 wherein n is 6.
8. A method of claim 1 wherein n is 7.
9. A method of claim 1 wherein n is 8.

* * * * *